(12) United States Patent
Maalouf et al.

(10) Patent No.: US 6,678,551 B2
(45) Date of Patent: Jan. 13, 2004

(54) METHOD AND APPARATUS FOR NOISE REDUCTION OF ELECTROMYOGRAM SIGNALS

(75) Inventors: Khalil John Maalouf, Clifton Park, NY (US); Yibin Zheng, Charlottesville, VA (US)

(73) Assignee: General Electric Company, Niskayuna, NY (US)

( * ) Notice: Subject to any disclaimer, the term of this patent is extended or adjusted under 35 U.S.C. 154(b) by 214 days.

(21) Appl. No.: 10/026,985

(22) Filed: Dec. 27, 2001

(65) Prior Publication Data

US 2003/0125635 A1 Jul. 3, 2003

(51) Int. Cl.[7] ................................. A61B 5/04
(52) U.S. Cl. ..................................... 600/546
(58) Field of Search .................. 600/546, 551, 600/588, 595, 596, 587, 300, 545; 128/905, 908

(56) References Cited

U.S. PATENT DOCUMENTS 3,905,355 A * 9/1975 Brudny ..................... 600/546
6,134,466 A * 10/2000 Rosenberg ................. 600/546

FOREIGN PATENT DOCUMENTS

EP    0568198 A2 * 11/1993  ........... G01R/19/25

OTHER PUBLICATIONS

*Adaptive Signal Processing*, Bernard Widrow, Samuel D. Sterns, Chapter 12, Adaptive Interference Canceling, 1985 by Prentice–Hall, Inc., pp. 327–337.

* cited by examiner

*Primary Examiner*—Max F. Hindenburg
*Assistant Examiner*—Brian Szmal
(74) *Attorney, Agent, or Firm*—Jean K. Testa; Patrick K. Patnode (57) ABSTRACT

A system and a method are provided for reducing noise in Electromyogram (EMG) signals from an external abdominal surface to detect uterine contractions. The system comprises an EMG1 sensor configured to detect a first EMG signal and to generate a corresponding EMG1 input signal and an EMG2 sensor configured to detect a second EMG signal and to generate a corresponding EMG2 input signal. A signal processor is coupled to the EMG1 sensor and the EMG2 sensor. The signal processor processes the EMG1 input signal and the EMG2 input signal with a filter and sum technique to generate an EMG1 reduced noise signal that represents a magnitude of at least one contraction event and periodicity of a set of multiple contraction events.

41 Claims, 4 Drawing Sheets

METHOD AND APPARATUS FOR NOISE REDUCTION OF ELECTROMYOGRAM SIGNALS

BACKGROUND

The present invention relates generally to reducing the noise in physiological signals. In particular the present invention relates to monitoring the medical condition of a woman in labor and to reducing the signal noise while processing abdominal surface electromyogram (EMG) signal data for the purpose of uterine contraction monitoring.

The present technology for monitoring uterine contraction uses a tocodynamometer, which measures the abdominal pressure exerted on a belt placed around the lower abdomen of a patient in labor. However, the tocodynamometer can be uncomfortable for some patients to wear. Additionally, abdominal pressure changes can be harder to detect on larger women. Enhanced uterine contraction monitoring through processing abdominal surface EMG signal data promises to provide obstetricians with an improved tool to diagnose whether a patient is at risk of preterm labor. Because premature birth is the leading cause (85%) of infant death, improved abdominal surface EMG technology holds the potential to advance prenatal care and management.

It has been well established that uterine contractions are caused by electrical potentials generated and propagated by muscle cells. These electrical activities occur in bursts and give rise to measurable electric fields called electromyographic (EMG) signals. The amplitude, frequency, and duration, of certain features of the EMG signals correspond to the frequency, duration, and effectiveness of the uterine contractions. The temporal and spectral characteristics of an EMG signal, recorded by external electrodes, make it possible to discriminate between efficient and inefficient contractions in terms of electrical command capability. It is also reported that the spectral density of the EMG signals shifts significantly at different stages during gestation, providing a means of separating non-laboring contractions from laboring contractions. It is possible to record uterine electrical activity as early as a gestational age of 19 weeks. Therefore, an abdominal EMG signal can be of value for pregnancy monitoring.

It is known that the EMG signal can be reliably recorded by placing electrodes on the internal uterine surface. However, such a procedure is both invasive and not accepted in clinical use. It has been proposed that the EMG signals should be acquired on the exterior surface of the abdomen, and this procedure has been shown to work in practice. EMG signals acquired in from the exterior surface of the abdomen can be used to detect and monitor contractions, due to the relationship between the onset of contraction and the spectral characteristics of the EMG signal. The main obstacles to such a use of EMG technology are, first, patient motion which causes noise and signal artifacts, second, interference from other physiological electrical events (such as Electrocardiogram (ECG)), and, third, imperfect electrode contacts.

There is a need for an effective means of reducing noise and more accurately processing the EMG signals received by the electrodes attached on the external abdominal wall, in order to extract from the EMG signal an indication of when the periods of contraction occur.

SUMMARY

Briefly, in accordance with one embodiment of the present invention, a system is provided for reducing noise in electromyogram (EMG) signals acquired from the external abdominal surface to determine uterine contractions. The system comprises an EMG1 sensor configured to detect a first EMG signal and to generate a corresponding EMG1 input signal and an EMG2 sensor configured to detect a second EMG signal and to generate a corresponding EMG2 input signal. A signal processor is coupled to the EMG1 sensor and the EMG2 sensor. The signal processor processes the EMG1 input signal and the EMG2 input signal with a filter and sum technique to technique to generate an EMG1 reduced noise signal that represents a magnitude of at least one contraction event and periodicity of a set of multiple contraction events.

In accordance with another embodiment of the present invention, a method is provided for processing the first EMG signal and the second EMG signal from an abdominal surface to detect uterine contractions. The method comprises detecting the first EMG signal and generating the EMG1 input signal and detecting a second EMG signal and generating the EMG2 input signal. Processing the EMG1 input signal and the EMG2 input signal using the filter and sum technique to generate the EMG1 reduced noise signal.

DRAWINGS

These and other features, aspects, and advantages of the present invention will become better understood when the following detailed description is read with reference to the accompanying drawings in which like characters represent like parts throughout the drawings, wherein.

DESCRIPTION

Although the physiology of uterine EMG generation is understood to a large degree, modeling the EMG waveform based on the underlying physiological process has proven to be difficult. The EMG input signal demonstrates the characteristics of a non-stationary random process; therefore, a phenomenological approach is employed. Furthermore, the EMG input signal acquired by the external abdominal electrodes is prone to noise artifacts that render the extraction of uterine contraction information for labor monitoring from such signals extremely difficult.

Figure 1:
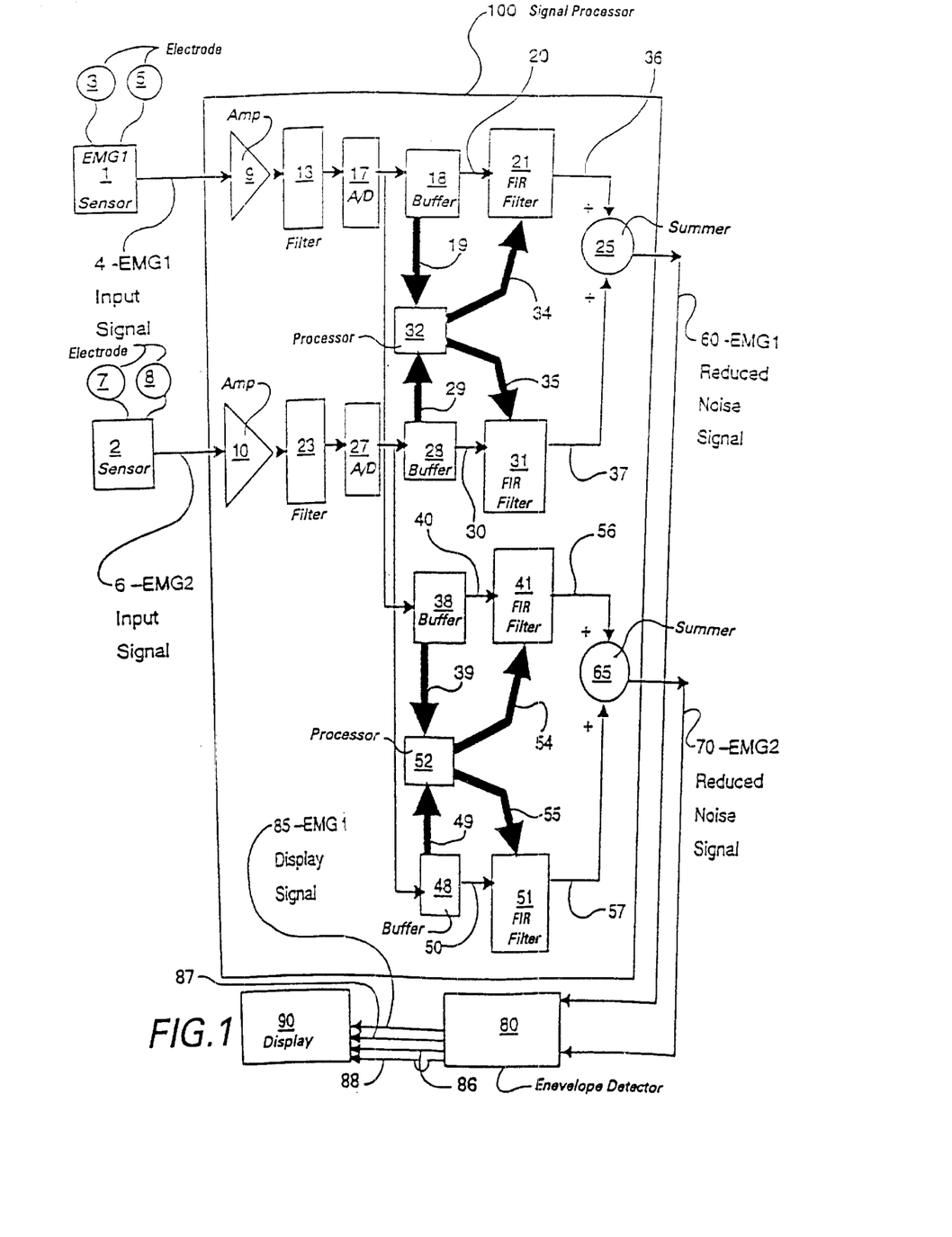
FIG. 1 is an overall block diagram representing a Uterine Contraction Monitoring System in accordance with one embodiment of the present invention.

In one embodiment of the present invention, a system for processing EMG input signals from an external abdominal surface to detect uterine contractions comprises an (meaning at least one) EMG1 sensor 1 configured to detect a first EMG signal and to generate a corresponding EMG1 input signal 4 as shown in FIG. 1. The system further comprises an (meaning at least one) EMG2 sensor 2 configured to detect a second EMG signal and to generate a corresponding EMG2 input signal 6. The system further comprises a signal processor 100 coupled to the EMG1 sensor 1 and the EMG2 sensor 2. The signal processor 100 is configured to process the EMG1 input signal 4 and EMG2 input signal 6 with a filter and sum technique to generate an EMG1 reduced noise signal 60.

In one embodiment of the present invention, an alpha electrode 3 and a beta electrode 5 are positioned on the external abdominal surface adjacent the uterus and these electrodes are connected to the EMG1 sensor 1 as shown in FIG. 1. A charlie electrode 7 and a delta electrode 8 are connected to an EMG2 sensor 2. The EMG1 sensor 1 and EMG2 sensor 2 generate an EMG1 input signal 4 and an EMG2 input signal 6, respectively, as shown in FIG. 1. In an alternative embodiment of the present invention, the EMG1 sensor and the EMG2 sensor are configured to use three electrodes where, for illustration purposes only and not limitation, the alpha electrode 3 is connected to both the EMG1 sensor and EMG2 sensor, while the beta electrode 5 is connected to EMG1 sensor 1 and charlie electrode 7 is connected to EMG2 sensor 2. In another embodiment of the present invention, an at least one electrode coupled to the EMG1 sensor is positioned on an opposite side of the abdomen from where the another at least one electrode is positioned that is coupled to the EMG2 sensor.

The EMG1 input signal 4 and EMG2 input signal 6 are mathematically described by the following equations:

EMG1 input signal 4(*i*)=S1(*i*)+N1(*i*); and

EMG2 input signal 6(*i*)=S2(*i*)+N2(*i*);

where S1 and S2 are the desired signal components of the EMG1 input signal 4 and EMG2 input signal 6, respectively. The N1 and N2 are the noise components, representing additive artifacts and random noise, in the EMG1 input signal 4 and the EMG2 input signal 6, respectively. The index "i" denotes the time samples. The random noise and artifacts in the EMG1 input signal 4 and EMG2 input signal 6 are typically caused by patient movement, interference from other physiological signals, loose electrodes to skin contact, and electronic thermal noise. The desired signals S1 and S2 of the EMG1 input signal 4 and EMG2 input signal 6, respectively, are unlikely to be statistically correlated between EMG1 sensor 1 and EMG2 sensor 2 because of the spatial and the path medium diversity of the EMG1 input signal 4 and EMG2 input signal 6. However, the noise signals N1 and N2 are typically correlated in at least a subset of the bandwidth of the EMG1 input signal 4 and EMG2 input signal 6.

In one embodiment of the present invention, the approximation of the desired signal S1 ($\overline{S1}(i)$) is computed from the EMG1 input signal 4 and the EMG2 input signal 6 using a filter and sum technique. The EMG1 input signal 4 is processed through an EMG1 FIR (Finite Impulse Response) filter 21, while the EMG2 input signal 6 is processed through an EMG2 reduced noise FIR filter 31. An EMG1 FIR filter output signal 36 is added to an EMG2 reduced noise FIR filter output signal 37 in an EMG1 reduced noise signal summer 25 to compute an EMG1 Reduced Noise signal 60, which is an estimation of an actual EMG1 desired signal, S1, as described above. In another embodiment of the present invention, the approximations $\overline{S1}(i)$ and $\overline{S2}(i)$ of the desired signals S1 and S2, respectively, are computed from the EMG1 input signal 4 and EMG2 input signal 6, respectively by using the filter and sum technique. The EMG1 reduced noise signal 60 is computed as described above. The EMG1 input signal 4 is additionally processed through an EMG1 reduced noise FIR filter 41. The EMG2 input signal 6 is processed through an EMG2 FIR filter 51. An EMG2 FIR filter output signal 57 is added to an EMG1 reduced noise FIR filter output signal 56 in an EMG2 reduced noise signal summer 25 to compute an EMG2 reduced noise signal 70, which is an estimation of an actual EMG2 desired signal, S2 as described above.

Mathematically, the architecture is represented as:

$$\overline{S1}(i) = \sum_{j=0}^{K1-1} w_j^1 * EMG1(i-j) + \sum_{j=0}^{K2-1} w_j^2 * EMG2(i-j)$$

$$\overline{S2}(i) = \sum_{j=0}^{K3-1} q_j^1 * EMG1(i-j) + \sum_{j=0}^{K4-1} q_j^2 * EMG2(i-j)$$

where K1 represents the number of filter taps in the EMG1 FIR filter 21, K2 represents the number of filter taps in the EMG2 reduced noise FIR filter 31, K3 represents the number of filter taps in the EMG1 reduced noise FIR filter 41, K4 represents the number of filter taps in the EMG2 FIR filter 51, $\overline{S1}(i)$ is an approximation to the desired signal S1, $\overline{S2}(i)$ is an approximation to the desired signal S2, $w_j^1$ represents the filter weights for the EMG1 FIR filter 21, $w_j^2$ represents the filter weights for the EMG2 reduced noise FIR filter 31, $q_j^1$ represents the filter weights for the EMG1 reduced noise FIR filter 41, $q_j^2$ represents the filter weights for the EMG2 FIR filter 51, EMG1 (i–j) represents the EMG1 input signal 4 at time (i–j), and EMG2 (i–j) represents the EMG2 input signal 6 at time (i–j). In another embodiment of the present invention, the number of taps K1, K2, K3 and K4 in the FIR filters 21, 31, 41 and 51, respectively can have the same value without affecting the ability of the present invention to reduce the noise associated with the EMG1 input signal 4 and the EMG2 input signal 6.

In some embodiments, the signal processor 100 is coupled to an envelope detection processor 80. In a more specific configuration, the envelope detection processor 80 processes the EMG1 reduced noise signal 60 through an envelope detection method to generate an EMG1 display signal 85. In another alternative configuration, the envelope detection processor 80 is configured to generate an EMG2 display signal 86 by processing the EMG2 reduced noise signal 70 through an envelope detection method. In another embodiment of the present invention, the envelope detection processor 80 generates a processed version of the EMG1 reduced noise signal 60 and a processed version of the EMG2 reduced noise signal 70. The envelope detection processor 80 further processes the processed version of the EMG1 reduced noise signal 60 and the processed version of the EMG2 reduced noise signal 70 to generate a weighted average processed EMG display signal 87. Alternatively, the envelope detection processor 80 is configured to select the highest signal value of either of the processed version of the EMG1 reduced noise signal 60 or the processed version of the EMG2 reduced noise signal 70 to generate a processed EMG display signal 88. The envelope detection processor 80 is coupled to a display device 90, and the envelope detection processor 80 is configured to provide a display signal to the display device 90. As used herein, the term "display signal" comprises one or more of following signals: the EMG1 display signal 85, the EMG2 display signal 86, the weighted average processed EMG display signal 87, and the processed EMG display signal 88. Various methods of envelope detection are known to one skilled in the art to process the EMG1 reduced noise signal 60. One method of envelope detection utilizes an auto regression (AR) method, which is provided for illustration and in no way implies a limitation to the present invention. One exemplary method of envelope detection is provided in the commonly assigned patent application General Electric Docket No. RD-28331, Method and Apparatus for Uterine Contraction Monitoring Using Linear Predictive Modeling of Abdominal Surface EMG Signals, R. Hoctor et al., filed concurrently here with.

The signal processor 100 and the envelope detection processor 80 can be any form of signal processing device or devices, including, by way of example and not limitation, a standard microprocessor, a digital signal processor, or a programmable logic device. The display device 90 is identified by way of example and not limitation as a computer monitor, instrument display monitor, a bedside display monitor, printer, or a strip chart recorder.

In one embodiment of the present invention, the alpha electrode and the beta electrode 5 are configured so as to detect the first EMG signal on the exterior abdominal surface adjacent to the uterus, while the charlie electrode 7 and delta electrode 8 are configured so as to detect the second EMG signal on the exterior abdominal surface adjacent to the uterus. Alternate electrode arrangements are discussed above. The signals from each pair of electrodes coupled to the EMG1 sensor are typically differentially compared in EMG1 sensor 1. The signals from each pair of electrodes coupled to the EMG2 sensor are typically differentially compared in EMG2 sensor 2. The difference between each pair of electrode outputs coupled to the EMG1 sensor 1 and each pair of electrode outputs coupled to the EMG2 sensor 2 is the output of EMG1 sensor 1 and EMG sensor 2, respectively, which corresponds to the EMG1 input signal 4 and the EMG2 input signal 6. In one alternative embodiment of the present invention, multiple pairs of electrodes are coupled to EMG1 sensor 1. In an alternative embodiment of the present invention, multiple pairs of electrodes are coupled to multiple EMG sensors to generate multiple EMG input signals that are then processed to produce multiple EMG reduced noise signals. The electrodes that were attached to the EMG1 sensor 1 and the EMG2 sensor 2 are able to detect the uterine EMG signals while mounted to an external abdominal surface adjacent the uterus. In one embodiment of the present invention, EKG electrodes were utilized to comprise each of the electrodes coupled to the EMG1 sensor 1 and the EMG2 sensor 2. One skilled in the art is knowledgeable in the use of EKG and EMG electrodes, and both the EKG and EMG electrodes are generally widely available. The specific use of either EKG or EMG electrodes is provided for illustration and is not intended to imply a limitation on the present invention.

In one embodiment of the present invention, the signal processor 100 typically further comprises the following components to generate the EMG1 reduced noise signal 60 and the EMG2 reduced noise signal 70. EMG1 amplifier 9 and EMG2 amplifier 10 amplify the EMG1 input signal 4 and EMG2 input signal 6, respectively. The EMG1 amplifier 9 and EMG2 amplifier 10 are coupled to EMG1 band pass filter 13 and EMG2 band pass filter 23, respectively. The EMG1 band pass filter 13 and EMG2 band pass filter 23 perform anti-aliasing filtering of the EMG1 input signal 4 and the EMG2 input signal 6, respectively. The EMG1 band pass filter 13 and EMG2 band pass filter 23 are coupled to EMG1 analog-to-digital converter 17 and EMG2 analog-to-digital converter 27, respectively. The EMG1 analog-to-digital converter 17 and EMG2 analog-to-digital converter 27 produce a digitized representation of the EMG1 input signal 4 and a digitized representation of the EMG2 input signal 6, respectively, at a typical sampling frequency range from about 0.01 Hz to about 200 Hz. In another embodiment of the present invention, the EMG1 analog-to-digital converter 17 and EMG2 analog-to-digital converter 27 produce a digitized representation of the EMG1 input signal 4 and a digitized representation of the EMG2 input signal 6, respectively, at a typical sampling frequency range from about 0.01 Hz to about 3 Hz.

In a more specific embodiment for obtaining EMG1 reduced noise signal 60, the EMG1 analog-to-digital converter 17 is coupled to an EMG1 input signal buffer 18. The EMG1 input signal buffer 18 generates an EMG1 buffer parallel output signal 19 and the EMG1 input signal buffer 18 is configured to send the EMG1 buffer parallel output signal 19 to the EMG1 adaptation computation processor 32. The EMG1 input signal buffer 18 also generates an EMG1 buffer serial output signal 20 and is further configured to send the EMG1 buffer serial output signal 20 to the EMG1 FIR filter 21. As used herein, the term "parallel" with respect to a type of signal, refers to a signal that concurrently transmits all information in the a device, and the term "serial" with respect to a type of signal, refers to a signal that concurrently transmits information in the device in a first in first out sequence. The EMG1 adaptation computation processor 32 is coupled to the EMG1 FIR filter 21 and is configured to generate an EMG1 FIR filter weight adjustment parallel signal 34. The EMG1 FIR filter 21 is configured to generate an EMG1 FIR output signal 36 and is coupled to the EMG1 reduced noise signal summer 25.

The EMG2 analog-to-digital converter 27 is coupled to an EMG2 reduced noise buffer 28. The EMG2 reduced noise buffer 28 generates an EMG2 reduced noise buffer parallel output signal 29 and the EMG2 reduced noise buffer 28 is configured to send the EMG2 reduced noise buffer parallel output signal 29 to the EMG1 adaptation computation processor 32. The EMG2 reduced noise input signal buffer 28 also generates an EMG2 reduced noise buffer serial output signal 30, and is further configured to send the EMG2 reduced noise buffer serial output signal 30 to the EMG2 reduced noise FIR filter 31. The EMG1 adaptation computation processor 32 is coupled to the EMG2 reduced noise FIR filter 31 and is configured to generate an EMG2 reduced noise FIR filter weight adjustment parallel signal 35.

EMG1 adaptation computation processor 32 is typically used to operate a constrained power reduction (minimization) technique to generate a set of weight coefficients for each filter tap in the EMG1 FIR filter 21 and the EMG2 reduced noise FIR filter 31. The EMG1 adaptation computation processor 32 typically computes the weight coefficients $w_j^1$ of the EMG1 FIR filter 21, such that one weight coefficient in one filter tap is set to a value of one (1) and the weight coefficients in the rest of the filter taps of the EMG1 FIR filter 21 are set to a value of zero (0), resulting in an all pass condition for the EMG1 input signal 4. The EMG1 FIR filter 21 produces an "all pass condition" if it passes the EMG1 input signal 4 with all frequencies, optionally with phase shift, but with no amplitude change in the EMG1 input signal 4. The values of the weight coefficients $w_j^1$ of the EMG1 FIR filter 21 can be selected in a different manner, so that the values of the weight coefficients $w_j^1$ are not restricted to values of 1 and 0, as long as the EMG1 FIR filter 21 passes the approximation $\overline{S1}(i)$ of the S1 desired signal of the EMG1 input signal 4. The frequency response of the EMG1 reduced noise signal 60 is typically in a range between about 0.01 Hz and about 3 Hz. The EMG1 adaptation computation processor 32 adapts the weight coefficients $w_j^2$ of the filter taps in the EMG2 reduced noise FIR filter 31 so as to reduce an EMG1 desired signal power performance index (P1), which is represented by the following:

$$\sum_{i=1}^{P1} (\overline{S1}(i))^2.$$

In this manner, the EMG1 reduced noise signal 60 provides the estimate of the actual primary EMG1 desired signal S1, where any statistically correlated noise components that are shared between the EMG1 input signal 4 and EMG2 input signal 6 are eliminated. The EMG1 adaptation computation processor 32 utilizes, by way of example and not limitation, the LMS (Least Mean Square) adaptation algorithm that adapts the weight coefficients of the filter taps in the EMG2 reduced noise FIR filter 31. The EMG2 reduced noise FIR filter 31 is configured to generate an EMG2 reduced noise FIR output signal 37 and is coupled to the EMG1 reduced noise signal summer 25. The EMG1 FIR output signal 36 and the EMG2 reduced noise FIR filter output signal 37 are added together in the EMG1 reduced noise signal summer 25 to generate the EMG1 reduced noise signal 60. In this manner, the EMG1 reduced noise signal 60 provides the estimate of the actual primary EMG1 desired signal S1, where any statistically correlated noise components that are shared between the EMG1 input signal 4 and EMG2 input signal 6 are eliminated.

In one embodiment for obtaining EMG2 reduced noise signal 70, the EMG2 analog-to-digital converter 27 is coupled to an EMG2 input signal buffer 48. The EMG2 input signal buffer 48 generates an EMG2 buffer parallel output signal 49 and the EMG2 input signal buffer 48 is configured to send the EMG2 buffer parallel output signal 49 to the EMG2 adaptation computation processor 52. The EMG2 input signal buffer 48 also generates an EMG2 buffer serial output signal 50, and is further configured to send the EMG2 buffer serial output signal 50 to the EMG2 FIR filter 51. The EMG2 adaptation computation processor 52 is coupled to the EMG2 FIR filter 51 and is configured to generate an EMG2 FIR filter weight adjustment parallel signal 55. The EMG2 FIR filter 51 is configured to generate an EMG2 FIR output signal 57 and is coupled to the EMG2 reduced noise signal summer 65.

The EMG1 analog-to-digital converter 17 is also coupled to an EMG1 reduced noise buffer 38. The EMG1 reduced noise buffer 38 generates an EMG1 reduced noise buffer parallel output signal 39 and the EMG1 reduced noise buffer 38 is configured to send the EMG1 reduced noise buffer parallel output signal 39 to the EMG2 adaptation computation processor 52. The EMG1 reduced noise buffer 38 also generates an EMG1 reduced noise buffer serial output signal 40, and is further configured to send the EMG1 reduced noise buffer serial output signal 40 to the EMG1 reduced noise FIR filter 41. The EMG2 adaptation computation processor 52 is coupled to the EMG1 reduced noise FIR filter 41 and is configured to generate an EMG1 reduced noise FIR filter weight adjustment parallel signal 54. The EMG2 adaptation computation processor 52 operates a constrained power reduction technique to generate a set of weight coefficients for each filter tap in the EMG1 reduced noise FIR filter 41 and the EMG2 FIR filter 51. The EMG2 adaptation computation processor 52 computes the weight coefficients $q_j^2$ of the EMG2 FIR filter 51, such that one weight coefficient in one filter tap is set to a value of one (1) and the weight coefficients in the rest of the filter taps of the EMG2 FIR filter 51 are set to a value of zero (0), resulting in an all pass condition for the EMG2 input signal 6. The EMG2 FIR filter 51 produces an "all pass condition" if it passes the EMG2 input signal 6 with all frequencies, optionally with phase shift, but with no amplitude change in the EMG2 input signal 6. The values of the weight coefficients $q_j^2$ of the EMG2 FIR filter 51 can be selected in a different manner, so that the values of the weight coefficients $q_j^2$ are not restricted to values of 1 and 0, as long as it results the EMG2 FIR filter 51 passes the approximation $\overline{S2}(i)$ of the S2 desired signal of the EMG2 input signal 6. The frequency response of the EMG2 reduced noise signal 70 is in a range between about 0.01 Hz and about 3 Hz. The EMG2 adaptation computation processor 52 adapts the weight coefficients $q_j^1$ of the filter taps in the EMG1 reduced noise FIR filter 41 so as to reduce an EMG2 desired signal power performance index (P2), which is represented by the following:

$$\sum_{i=1}^{P2} (\overline{S2}(i))^2.$$

In one embodiment of the present invention, the EMG2 adaptation computation processor 52 comprises the LMS adaptation algorithm that adapts the weight coefficients of the filter taps in the EMG1 reduced noise FIR filter 41. The EMG1 reduced noise FIR filter 41 is configured to generate an EMG1 reduced noise FIR output signal 56 and is coupled to an EMG2 reduced noise signal summer 65. The EMG1 reduced noise FIR output signal 56 and the EMG2 FIR filter output signal 57 are added together in the EMG2 reduced noise signal summer 65 to generate the EMG2 reduced noise signal 70. In this manner, the EMG2 reduced noise signal 70 provides the estimate of the actual primary EMG2 desired signal S2, where any statistically correlated noise components that are shared between the EMG1 input signal 4 and EMG2 input signal 6 are eliminated.

In one embodiment of the present invention, both the EMG1 reduced noise signal summer 25 and the EMG2 reduced noise summer 65 are typically coupled to an envelope detection processor 80. The EMG1 reduced noise signal summer 25 is also configured to pass the EMG1 reduced noise signal 60 to the envelope detection processor 80. The EMG2 reduced noise signal summer 65 is also configured to pass the EMG2 reduced noise signal 70 to the envelope detection processor 80.

In one embodiment of the present invention, the EMG1 adaptation computation processor 32 updates the weight coefficient for each corresponding filter tap in the EMG1 FIR filter 21 and the EMG2 reduced noise FIR filter 31 with each new data sample using, by way of example and not limitation, the LMS adaptation algorithm and the EMG2 adaptation computation processor 52 updates the weight coefficient for each corresponding filter tap in the EMG1 reduced noise FIR filter 41 and the EMG2 FIR filter 51 with each new data sample using, by way of example and not limitation, the LMS adaptation algorithm. Any standard method of estimation of the AR (auto regression) parameters would also be acceptable. The present invention is by no means limited to the use of the LMS adaptation algorithm. In another embodiment, the EMG1 adaptation computation processor 32 updates the weight coefficient for each corresponding filter tap in the EMG1 FIR filter 21 and the EMG2 reduced noise FIR filter 31 and the EMG2 adaptation computation processor 52 updates the weight coefficient for each corresponding filter tap in the EMG1 reduced noise FIR filter 41 and the EMG2 FIR filter 51 using a buffered data technique. In a buffered data technique the weight coefficients of the corresponding filter taps are calculated based on a set of data, and act on the same data or possibly another set of data.

Figure 2:
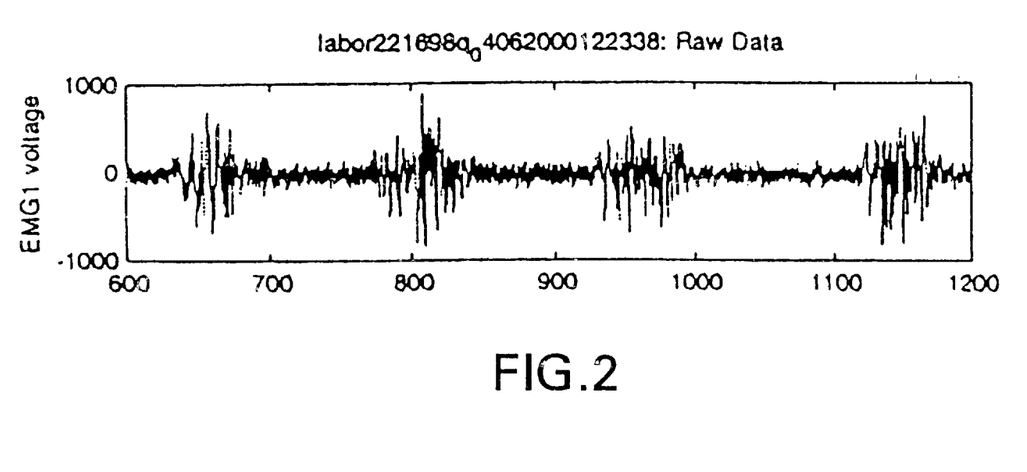
FIG. 2 is a graphic representation of responses of an EMG1 input signal to one set of uterine contraction events.
Figure 3:
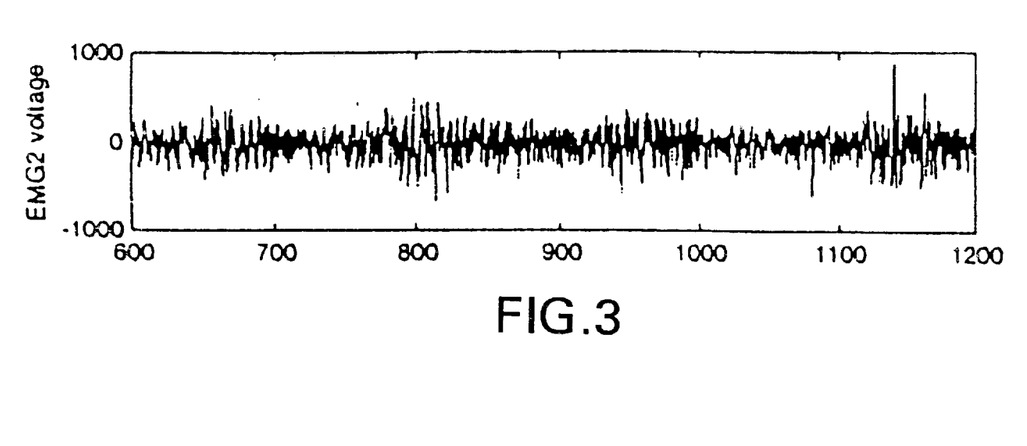
FIG. 3 is a graphic representation of responses of an EMG2 input signal to one set of uterine contraction events.
Figure 4:
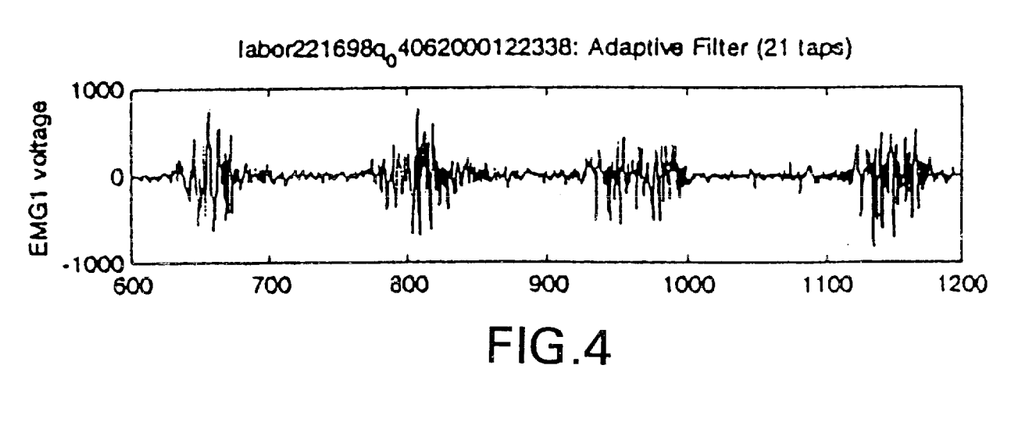
FIG. 4 is a graphic representation of responses of an EMG1 reduced noise signal to one set of uterine contraction events.
Figure 5:
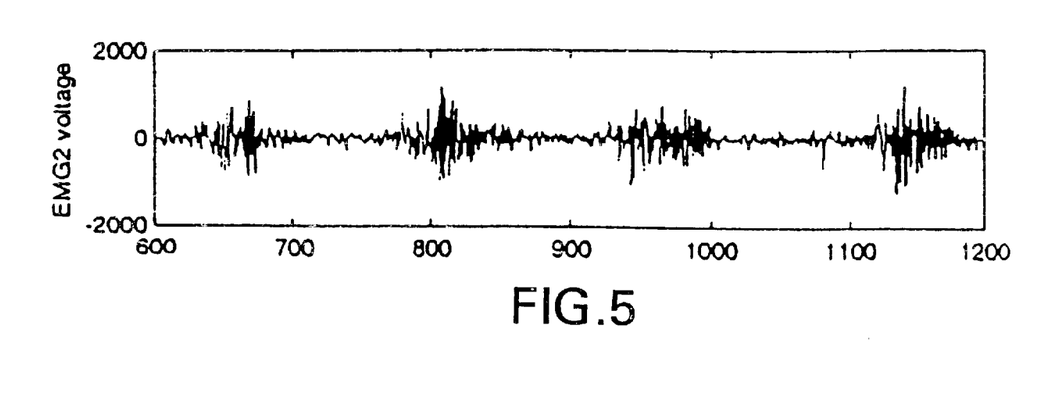
FIG. 5 is a graphic representation of responses of an EMG2 reduced noise signal to one set of uterine contraction events.
Figure 6:
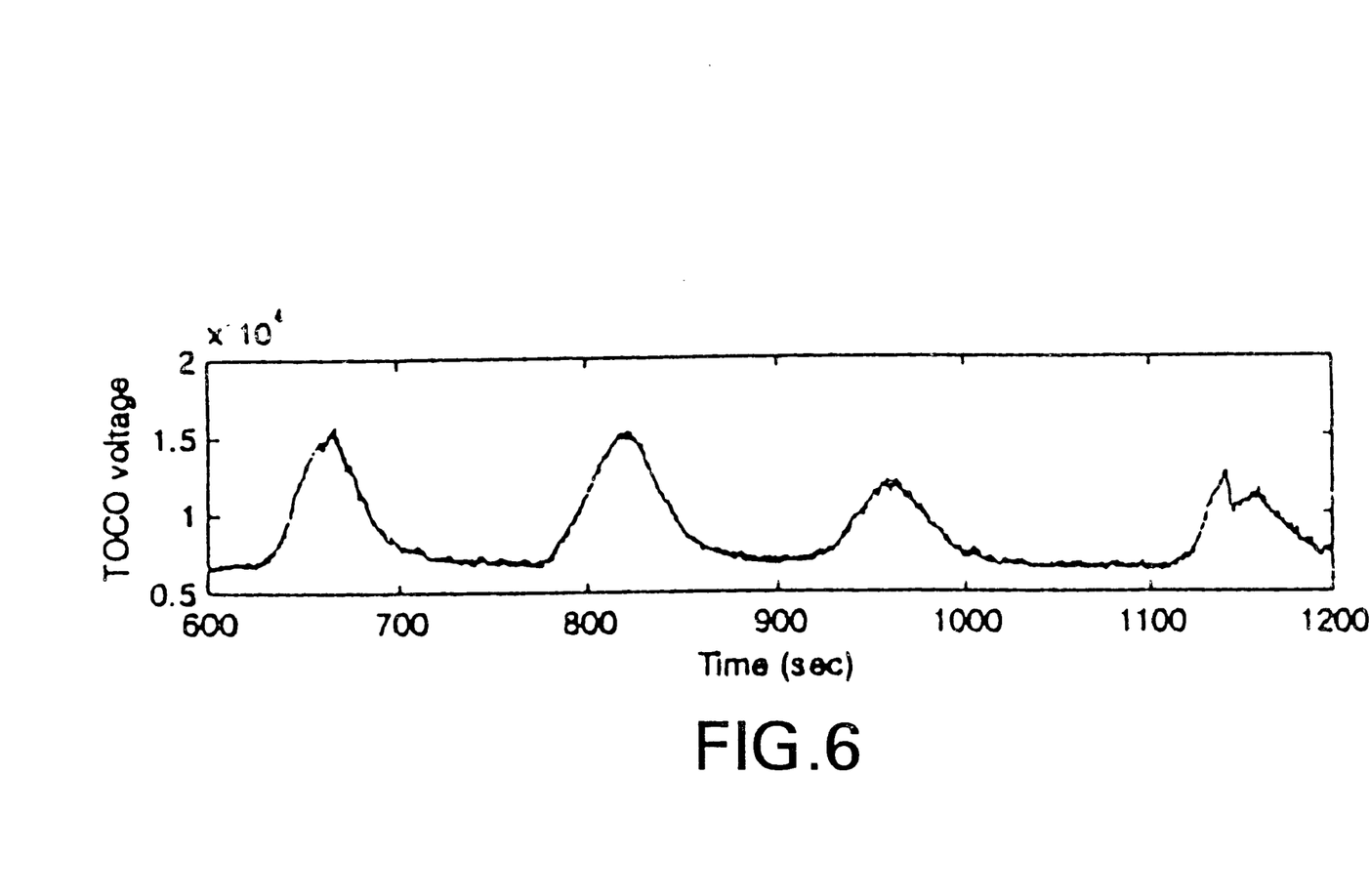
FIG. 6 is a graphic representation of responses of display signal to one set of uterine contraction events.

As an example of the processing just described, the response of the digitized version of the EMG1 input signal 4 and the response of the digitized version of the EMG2 input signal 6 to a set of uterine contraction events are provided in FIGS. 2 and 3, respectively. A response to the same set of uterine contraction events used to generate FIGS. 2 and 3 that represents the EMG1 reduced noise signal 60 is depicted in FIG. 4. A response to the same set of uterine contraction events used to generate FIGS. 2, 3 and 4 that represents the EMG2 reduced noise signal 70 is depicted in FIG. 5. FIGS. 4 and 5 were generated using the buffered data technique described above. A response to the same set of uterine contraction events used to generate FIGS. 2, 3, 4 and 5 is provided by the weighted average processed EMG display signal 87 as depicted in FIG. 6. The weighted average processed EMG display signal 87 displayed in FIG. 6 is generated as discussed above. The sampling frequency of the digitized representation of the EMG1 input signal 4 and the digitized representation of the EMG2 input signal 6 has a typical range between about 1 Hz and about 200 Hz. Both the EMG1 reduced noise signal 60 as depicted in FIG. 5 and the EMG2 reduced noise signal 70 as depicted in FIG. 6 were generated when the digitized representation of the EMG1 input signal 4 and the digitized representation of the EMG2 input signal 6 sampling frequency was four (4) Hz.

In another embodiment of the present invention, the LMS adaptation algorithm is used, the FIR filters 21, 31, 41 and 51 are configured with 21 model orders, and both the digitized representation of the EMG1 input signal 4 and the digitized representation of the EMG2 input signal 6 have a sampling frequency rate in a typical range between about 1 Hz and about 200 Hz.

In one embodiment of the present invention, the LMS adaptation algorithm is utilized, the FIR filters 21, 31, 41 and 51 are configured with 21 model orders, and both the digitized representation of the EMG1 input signal 4 and the digitized representation of the EMG2 input signal 6 have a sampling frequency rate of 4 Hz.

A specific embodiment of a method and apparatus for reducing the noise in external abdominal surface EMG signal data for the purpose of detecting uterine contractions according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A system for processing electromyogram (EMG) input signals from an external abdominal surface to detect uterine contractions, said system comprising:
    an EMG1 sensor configured to detect a first EMG signal and to generate a corresponding EMG1 input signal;
    an EMG2 sensor configured to detect a second EMG signal and to generate a corresponding EMG2 input signal; and
    a signal processor coupled to said EMG1 sensor and said EMG2 sensor, said signal processor being configured to process said EMG1 input signal and said EMG2 input signal with a filter and sum technique to generate an EMG1 reduced noise signal that represents a magnitude of at least one uterine contraction event and periodicity of a set of multiple uterine contraction events.

2. The system of claim 1 further comprising:
    an envelope detection processor configured to process said EMG1 reduced noise signal to generate an EMG1 display signal representing said magnitude of at least one said uterine contraction event and said periodicity of said set of multiple contraction events.

3. The system of claim 2 further comprising a display device coupled to said envelope detection processor, wherein said display device is configured to display said EMG1 display signal.

4. The system of claim 2, wherein said envelope detection processor is configured to process said EMG1 reduced noise signal by utilizing a envelope detection method including auto regression.

5. The system of claim 1, said signal processor further comprising:
    an EMG1 adaptation computation processor;
    an EMG1 Finite Impulse Response (FIR) filter; and
    an EMG2 reduced noise FIR filter,
    wherein said EMG1 adaptation computation processor is configured to operate a constrained power reduction technique to generate weight coefficients for filter taps in said EMG1 FIR filter and in said EMG2 reduced noise FIR filter; said weight coefficients of said EMG1 FIR filter being selected to preserve a desired signal in said EMG1 reduced noise signal, said weight coefficients of said EMG2 reduced noise FIR filter being selected to reduce output power.

6. The system of claim 5, wherein said EMG1 FIR filter and said EMG2 reduced noise FIR filter have a model order number of at least 2.

7. The system of claim 5, wherein a digitized representation of said EMG1 input signal and a digitized representation of said EMG2 input signal have a sampling frequency range from about 1 Hz to about 200 Hz, and said EMG1 reduced noise signal has a frequency response range from about 0.01 Hz to about 3 Hz.

8. The system of claim 5, wherein said EMG1 FIR filter and said EMG2 reduced noise FIR filter have a model order number of about 21 and a digitized representation of said EMG1 input signal and a digitized representation of said EMG2 input signal have a sampling frequency of about 4 Hz.

9. The system of claim 5, wherein said EMG1 adaptation computation processor is configured to utilize an auto regression method to determine said weight coefficients of said EMG1 FIR filter and said EMG2 reduced noise FIR filter.

10. The system of claim 9, wherein said auto regression method uses a Least Mean Square adaptation algorithm.

11. The system of claim 9, wherein said auto regression method uses a buffered data technique.

12. The system of claim 1, wherein said signal processor is further configured to process said EMG1 input signal and said EMG2 input signal with said filter and sum technique to generate an EMG2 reduced noise signal and further comprising;
    an envelope detection processor, configured to independently process said EMG1 reduced noise signal and said EMG2 reduced noise signal through an envelope detection method to generate an EMG1 display signal and an EMG2 display signal each of which represents a magnitude of at least one uterine contraction event and periodicity of a set of multiple uterine contraction events.

13. The system of claim 12, further comprising;

a display device;

wherein said display device is coupled to said envelope detection processor, wherein said display device is configured to display at least one of said EMG1 display signal and said EMG2 display signal.

14. The system of claim 12, wherein said envelope detection processor is further configured to generate a processed version of said EMG1 reduced noise signal and a processed version of said EMG2 reduced noise signal, wherein said envelope detection processor is further configured to process said processed version of EMG1 reduced noise signal and said processed version of EMG2 reduced noise signal to generate a weighted average processed EMG display signal.

15. The system of claim 14, further comprising:

a display device;

wherein said display device is configured to be coupled to said envelope detection processor, wherein said display device is configured to display at least one of said EMG1 display signal, said EMG2 display signal, and said weighted average processed EMG display signal.

16. The system of claim 12, wherein said envelope detection processor is further configured to generate a processed version of said EMG1 reduced noise signal and a processed version of said EMG2 reduced noise signal, wherein said envelope detection processor is further configured to generate a processed EMG display signal which comprises a highest signal value of said processed version of said EMG1 reduced noise signal and said processed version of said EMG2 reduced noise signal.

17. The system of claim 16, further comprising:

a display device;

wherein said display device is configured to be coupled to said envelope detection processor, wherein said display device is configured to display at least one of said EMG1 display signal, said EMG2 display signal and said processed EMG display signal.

18. The system of claim 1, said signal processor further comprising:

an EMG2 adaptation computation processor;

an EMG1 reduced noise FIR filter; and an EMG2 FIR filter, wherein said EMG2 adaptation computation processor is configured to operate a constrained power reduction technique to generate of weight coefficients for filter taps in said EMG1 reduced noise FIR filter and in said EMG2 FIR filter; said weight coefficients of said EMG2 FIR filter being selected to preserve a desired signal in said EMG2 reduced noise signal, said weight coefficients of said EMG1 reduced noise FIR filter being selected to reduce output power.

19. The system of claim 18, wherein said EMG2 FIR filter and said EMG1 reduced noise FIR filter have a model order number of at least 2.

20. The system of claim 18, wherein a digitized representation of said EMG2 input signal has a sampling frequency range from about 1 Hz to about 200 Hz, and said EMG2 reduced noise signal has a frequency response range from about 0.01 Hz to about 3 Hz.

21. The system of claim 18, wherein said EMG2 FIR filter and said EMG1 reduced noise FIR filter have a model order number of about 21 and a digitized representation of said EMG2 input signal has a sampling frequency of about 4 Hz.

22. The system of claim 18, wherein said EMG2 adaptation computation processor utilizes an auto regresion method to determine said weight coefficients of said EMG2 FIR filter and said EMG1 reduced noise FIR filter.

23. The system of claim 22, wherein said auto regression method uses a Least Mean Square adaptation algorithm.

24. The system of claim 22, wherein said auto regression method uses a buffered data technique.

25. The system of claim 1, wherein further comprising:

an alpha electrode;

a bravo electrode; and a charlie electrode, wherein said alpha electrode, said bravo electrode and said charlie electrode are configured to be placed in contact with said exterior abdominal surface adjacent to said uterus, wherein said alpha electrode and said bravo electrode are configured to be coupled to said EMG1 sensor to detect said first EMG signal, wherein said bravo electrode and said charlie electrode are configured to be coupled to said EMG2 sensor to detect said second EMG signal.

26. The system of claim 1, wherein further comprising:

an alpha electrode;

a bravo electrode;

a charlie electrode; and a delta electrode, wherein said alpha electrode, said beta electrode, said charlie electrode and said delta electrode are configured to be placed in contact with said exterior abdominal surface adjacent to said uterus, wherein said alpha electrode and said bravo electrode are configured to be coupled to said EMG1 sensor to detect said first EMG signal, wherein said charlie electrode and said delta electrode are configured to be coupled to said EMG2 sensor to detect said second EMG signal.

27. The system of claim 26, wherein said each of said electrodes is selected from the group consisting of an Electrocardiogram (EKG) electrode and an Electromyogram (EMG) electrode.

28. A method for processing electromyogram (EMG) input signals from an external abdominal surface to detect uterine contractions, said method comprising:

generating an EMG1 input signal;

generating an EMG2 input signal;

processing said EMG1 input signal and said EMG2 input signal with a filter and sum technique to generate an EMG1 reduced noise signal; and processing said EMG1 reduced noise signal with an envelope detection method to generate an EMG1 display signal, wherein said EMG1 display signal represents a magnitude of at least one uterine contraction event and periodicity of a set of multiple uterine contraction events.

29. The method of claim 28 further comprising the EMG1 display signal on a display device.

30. The method of claim 28, wherein a digitized representation of said EMG1 input signal and a digitized representation of said EMG2 input signal have a sampling frequency rate range from about 1 Hz to about 200 Hz and said EMG1 reduced noise signal has a frequency response range from about 0.01 Hz to about 3 Hz.

31. The method of claim 28, wherein processing said EMG1 input signal and said EMG2 input signal with said filter and sum technique to generate said EMG1 reduced noise signal further comprises the steps of:

operating a constrained power reduction technique to generate a set of weight coefficients for filter taps in an EMG1 FIR filter and in an EMG2 reduced noise FIR filter by selecting said weight coefficients of said EMG1 FIR filter, wherein a desired signal in said EMG1 reduced noise signal is preserved and selecting said weight coefficients of said EMG2 reduced noise FIR filter so as to reduce an output power.

32. The method of claim 31, wherein said EMG1 FIR filter and said EMG2 reduced noise FIR filter have a model number of at least 2.

33. The method of claim 28 further comprising the steps of:

processing said EMG1 input signal and said EMG2 input signal with a filter and sum technique to generate an EMG2 reduced noise signal; and processing said EMG2 reduced noise signal with an envelope detection method to generate an EMG2 display signal, wherein said EMG2 display signal represents a magnitude of at least one uterine contraction event and periodicity of a set of multiple uterine contraction events.

34. The method of claim 33 further comprising displaying the EMG2 display signal on a display device.

35. The method of claim 33, wherein said EMG2 reduced noise signal has a frequency response range from about 0.01 Hz to about 3 Hz.

36. The method of claim 33, wherein processing said EMG1 input signal and said EMG2 input signal with said filter and sum technique to generate an EMG2 reduced noise signal further comprises:

operating a constrained power reduction technique to generate a set of weight coefficients for filter taps in an EMG2 FIR filter and in an EMG1 reduced noise FIR filter, selecting said weight coefficients of said EMG2 FIR filter, wherein a desired signal in said EMG2 reduced noise signal is preserved; and selecting said weight coefficients of said EMG1 reduced noise FIR filter so as to reduce an output power.

37. The method of claim 36, wherein said EMG2 FIR filter and said EMG1 reduced noise FIR filter have a model number of at least 2.

38. The method of claim 33, further comprising:

processing said EMG1 reduced noise signal through an envelope detection method to generate a processed version of said EMG1 reduced noise signal;

processing said EMG2 reduced noise signal through an envelope detection method to generate a processed version of said EMG2 reduced noise signal; and processing said processed version of EMG1 reduced noise signal and said processed version of EMG2 reduced noise signal to generate a weighted average processed EMG display signal.

39. The method of claim 38 further comprising displaying said weighted average processed EMG display signal on a display device.

40. The method of claim 33, further comprising:

processing said EMG1 reduced noise signal through an envelope detection method to generate a processed version of said EMG1 reduced noise signal;

processing said EMG2 reduced noise signal through an envelope detection method to generate a processed version of said EMG2 reduced noise signal; and selecting a highest signal value of either said processed version of said EMG1 reduced noise signal or said processed version of said EMG2 reduced noise signal to generate to generate a processed EMG display signal.

41. The method of claim 40, further comprising displaying said processed EMG display signal on a display device.

* * * * *

UNITED STATES PATENT AND TRADEMARK OFFICE
CERTIFICATE OF CORRECTION

PATENT NO. : 6,678,551 B2
DATED : January 13, 2004
INVENTOR(S) : Khalil John Maalouf and Yibin Zheng It is certified that error appears in the above-identified patent and that said Letters Patent is hereby corrected as shown below:

Column 10,
Lines 6-11, should read:
    2. The system of claim 1 further comprising:
    an envelope detection processor configured to process said EMG1 reduced noise signal to generate an EMG1 display signal representing said magnitude of at least one said uterine contracting event and said periodicity of said set of multiple uterine contraction events.

Signed and Sealed this

Twenty-second Day of March, 2005

JON W. DUDAS
*Director of the United States Patent and Trademark Office*